(12) United States Patent
Huebner (10) Patent No.: US 8,231,662 B2
(45) Date of Patent: Jul. 31, 2012

(54) BONE FIXATION WITH A STRUT-STABILIZED BONE PLATE

(75) Inventor: Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 998 days.

(21) Appl. No.: 11/550,255

(22) Filed: Oct. 17, 2006

(65) Prior Publication Data

US 2008/0161861 A1    Jul. 3, 2008

(51) Int. Cl.
*A61B 17/80* (2006.01)

(52) U.S. Cl. ........... 606/280; 606/70; 606/71; 606/281; 606/283; 606/284

(58) Field of Classification Search .............. 606/70–71, 606/86 B, 101, 280–299, 902–906, 915
See application file for complete search history.

(56) References Cited

U.S. PATENT DOCUMENTS

| | | | |
|---|---|---|---|
| 1,025,008 A | 4/1912 | Miner | |
| 2,526,959 A * | 10/1950 | Lorenzo | 606/66 |
| 2,580,821 A | 1/1952 | Nicola | |
| 3,604,414 A | 9/1971 | Borges | |
| 3,842,825 A * | 10/1974 | Wagner | 606/66 |
| 4,187,841 A | 2/1980 | Knutson | |
| 4,794,918 A | 1/1989 | Wolter | |
| 4,903,691 A | 2/1990 | Heinl | |
| 4,905,679 A | 3/1990 | Morgan | |
| 5,013,315 A | 5/1991 | Barrows | |
| 5,190,544 A * | 3/1993 | Chapman et al. | 606/71 |
| 5,250,048 A | 10/1993 | Gundolf | |
| 5,470,333 A * | 11/1995 | Ray | 606/261 |
| 5,634,926 A * | 6/1997 | Jobe | 606/281 |
| 5,665,089 A | 9/1997 | Dall et al. | |
| 5,707,372 A | 1/1998 | Errico et al. | |
| 5,741,259 A | 4/1998 | Chan | |
| 5,749,873 A | 5/1998 | Fairley | |
| 5,752,958 A | 5/1998 | Wellisz | |
| 5,827,286 A | 10/1998 | Incavo et al. | |
| 5,853,413 A * | 12/1998 | Carter et al. | 606/281 |
| 5,964,763 A | 10/1999 | Incavo et al. | |
| 6,093,188 A | 7/2000 | Murray | |
| 6,096,040 A * | 8/2000 | Esser | 606/280 |

(Continued)

FOREIGN PATENT DOCUMENTS

DE    867422    2/1953

(Continued)

OTHER PUBLICATIONS

Copenheaver, Blaine R., Authorized officer, International Searching Authority, International Search Report, International Patent Application Serial No. PCT/US2007/022323; search date: Apr. 25, 2008.

(Continued)

*Primary Examiner* — Thomas Barrett
*Assistant Examiner* — Melissa A Golob
(74) *Attorney, Agent, or Firm* — Kolisch Hartwell, PC (57) ABSTRACT

A system and a method for bone fixation are provided. A bone plate may be secured to at least one bone. A monolithic region of the bone plate may be bent to a bent configuration. A strut may be connected to the bone plate. In some embodiments, the strut may be connected at spaced positions of the bone plate that opposingly flank the monolithic region, such that the bent configuration is stabilized.

18 Claims, 3 Drawing Sheets

U.S. PATENT DOCUMENTS

| | | | |
|---|---|---|---|
| 6,129,728 A * | 10/2000 | Schumacher et al. | 606/71 |
| 6,235,034 B1 | 5/2001 | Bray | |
| 6,238,396 B1 | 5/2001 | Lombardo | |
| 6,306,136 B1 | 10/2001 | Baccelli | |
| 6,325,803 B1 * | 12/2001 | Schumacher et al. | 606/71 |
| 6,336,927 B2 | 1/2002 | Rogozinski | |
| 6,355,036 B1 | 3/2002 | Nakajima | |
| 6,355,042 B2 * | 3/2002 | Winquist et al. | 606/283 |
| 6,364,881 B1 | 4/2002 | Apgar et al. | |
| 6,402,756 B1 | 6/2002 | Ralph et al. | |
| 6,413,259 B1 | 7/2002 | Lyons et al. | |
| 6,506,191 B1 * | 1/2003 | Joos | 606/86 B |
| 6,565,570 B2 | 5/2003 | Sterrett et al. | |
| 6,872,210 B2 * | 3/2005 | Hearn | 606/71 |
| 7,326,212 B2 | 2/2008 | Huebner | |
| 2002/0055741 A1 | 5/2002 | Schlapfer et al. | |
| 2002/0147453 A1 | 10/2002 | Gambale | |
| 2003/0060827 A1 | 3/2003 | Coughln | |
| 2003/0149434 A1 | 8/2003 | Paul | |
| 2004/0102775 A1 * | 5/2004 | Huebner | 606/69 |
| 2004/0102776 A1 * | 5/2004 | Huebner | 606/69 |
| 2004/0102777 A1 * | 5/2004 | Huebner | 606/69 |
| 2004/0102778 A1 | 5/2004 | Huebner et al. | |
| 2004/0158250 A1 | 8/2004 | Chappius | |
| 2004/0220566 A1 | 11/2004 | Bray | |
| 2005/0085819 A1 | 4/2005 | Ellis et al. | |
| 2005/0234458 A1 * | 10/2005 | Huebner | 606/69 |
| 2005/0240187 A1 | 10/2005 | Huebner et al. | |
| 2006/0089648 A1 * | 4/2006 | Masini | 606/69 |
| 2006/0116679 A1 * | 6/2006 | Lutz et al. | 606/69 |
| 2006/0161158 A1 * | 7/2006 | Orbay et al. | 606/69 |
| 2007/0185493 A1 | 8/2007 | Feibel et al. | |

FOREIGN PATENT DOCUMENTS

| | | |
|---|---|---|
| EP | 773004 | 5/1997 |
| EP | 0773004 | 5/1997 |
| EP | 829240 | 3/1998 |
| EP | 1308135 | 5/2003 |
| FR | 1239266 | 7/1960 |
| WO | 2004045455 | 6/2004 |

OTHER PUBLICATIONS

Copenheaver, Blaine, Authorized officer, International Searching Authority, Written Opinion of the International Searching Authority, International Patent Application Serial No. PCT/US2007/022323; completion date: Apr. 25, 2008.

* cited by examiner

BONE FIXATION WITH A STRUT-STABILIZED BONE PLATE

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, fractured bones are treated using fixation devices, which reinforce the fractured bones and keep them aligned during healing. Fixation devices may take a variety of forms, including casts for external fixation, and bone plates, bone screws, and/or wires for internal fixation, among others.

Bone plates are sturdy internal devices, usually made of metal, that mount directly to the bone adjacent a fracture (or other bone discontinuity). To use a bone plate to repair a fractured bone, a surgeon typically (1) selects an appropriate plate, (2) reduces the fractured bone (e.g., sets the fracture), and (3) fastens the plate to bone fragments disposed on opposing sides of the fracture using suitable fasteners, such as bone screws, so that the bone plate spans the fracture and the bone fragments are fixed in position.

A surgeon using a bone plate often may have difficulty fixing a fractured bone with the desired alignment of bone fragments. For example, the bone fragments may be relatively small and/or somewhat inaccessible surgically. In addition, bone screws that fasten the bone plate to bone may be misplaced or misdirected so that the bone fragments move out of a properly reduced arrangement as the bone screws are tightened.

In some cases, it may be possible to improve the reduction of a fractured bone by bending a bone plate after the bone plate has been secured to the fractured bone. For example, U.S. patent application Ser. No. 10/717,402, filed Nov. 19, 2003, which is incorporated herein by reference, describes fixation systems in which bone plates may be bent after attachment to bone, to adjust the relative disposition of connected bone fragments. However, in some cases, these fixation systems may not be capable of providing a bone plate possessing a suitable combination of intraoperative bendability and post-operative strength.

SUMMARY

The present teachings provide a system, including methods, apparatus, and kits, for bone fixation using a bone plate and a strut that stabilizes the bone plate on bone.

DETAILED DESCRIPTION

The present teachings provide a system, including methods, apparatus, and kits, for bone fixation using a bone plate and a strut that stabilizes the bone plate on bone.

The bone plate may be structured for use with a strut and for use on any suitable bone, such as a distal portion of a radius bone, among others. In some examples, the bone plate may be generally T-shaped, such that when the bone plate is secured to bone, the bone plate has a more distally (or proximally) disposed, transverse head portion connected to a more proximally (or distally) disposed, longitudinal stem portion. In addition, the bone plate may be structured to be bent, after its manufacture, to a desired bent configuration (e.g., about a transverse axis (or axes) of the bone plate) before placement on bone. Alternatively, or in addition, the bone plate may be structured to be bent to a desired bent configuration (e.g., about a transverse axis (or axes) of the bone plate) after the bone plate is secured to bone, to adjust the alignment (e.g., the relative angular disposition) of bone fragments of the bone. The bone plate (and/or a region of the bone plate at which the bone plate is bent selectively) thus may be thinner, narrower, and/or more malleable than a corresponding standard bone plate for the same bone, to facilitate bending of the bone plate before and/or after placement on bone.

The strut may be structured to be connected to the bone plate for stabilization of each of a plurality of alternative bent configurations of the bone plate, or for stabilization of a distinct bent configuration of the bone plate. To facilitate stabilization, the strut and the bone plate may present mating structures that are generally complementary to one another, to promote assembly of the bone plate with the strut and/or to resist slippage of the strut relative to the bone plate after assembly. In some embodiments, the mating structures of the bone plate and strut may be configured to permit assembly of the strut and the bone plate in a plurality of discrete registers, to accommodate changes to the effective length of the bone plate produced by different bent configurations. Exemplary mating structures may include an array of projections (and/or depressions) formed on an outer (or inner) face of the bone plate and a corresponding array of depressions (and/or projections) formed on an inner (or outer) face of the strut. In any case, the strut and the bone plate may define one, two, or more respective pairs of openings, with each pair positioned for alignment and receipt of a fastener. Furthermore, the strut may be configured to increase the stability of the bone plate, such as by having a thickness and/or width that is greater than the corresponding average, maximum, and/or regional dimension of the bone plate, particularly a thickness and/or width of the strut that is greater than the thickness and/or width of a region of the bone plate that is bent intraoperatively. In any event, the strut may stabilize the bone plate against bending and/or twisting about any suitable transverse (i.e., generally crosswise) and/or longitudinal axes of the bone plate.

Overall, the fixation systems of the present teachings may offer significant advantages. These advantages may include, for example, improved control during reduction of fractured bones; bone plates that are bent more easily and/or formed with less material (and thus are less expensive); and/or better stabilization of a bendable bone plate (and thus a fractured bone); among others.

Further aspects of the present teachings are described in the following sections: (I) overview of an exemplary strut-stabilized fixation system, (II) bone plates, (III) struts, (IV) composition of system components, (V) methods of strut-stabilized bone fixation, (VI) kits, and (VII) examples.

I. OVERVIEW OF AN EXEMPLARY STRUT-STABILIZED FIXATION SYSTEM

Figure 1:
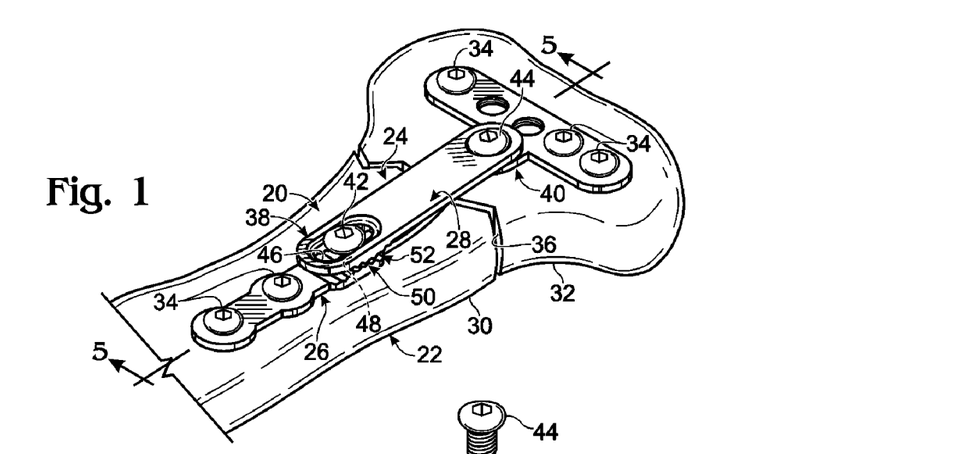
FIG. 1 is a volar-medial view of a fractured radius bone fixed distally with an exemplary fixation system including a bone plate stabilized by a strut, in accordance with aspects of the present teachings.

FIG. 1 shows an exemplary strut-stabilized fixation system 20 installed on the distal portion of a fractured radius bone 22. System 20 may include a fixation device or fixation assembly 24 composed of a bone plate 26 stabilized by a strut 28. The bone plate may be secured to fragments 30, 32 of the radius bone by bone fasteners 34, such as bone screws, to position the bone plate in a spanning relationship to a fracture 36 of the radius bone (or other suitable bone).

The strut may be secured to the bone plate to stabilize a selected bent configuration of the bone plate. For example, the strut may restrict the bone plate from bending longitudinally (i.e., about one or more transverse axes of the bone plate (e.g., a width axis of the bone plate)). Here, the bone plate is stabilized against out-of-plane bending of the bone plate about transverse axes of the bone plate disposed between connection sites 38, 40 at which the bone plate and strut engage one another. In other words, the bone plate is stabilized against bending that would change the profile of the bone plate. The strut also may stabilize the bone plate against twisting (e.g., bending about the long axis of the bone plate), although in some examples the strut may be less effective in providing stabilization against twisting. Accordingly, the term "stabilize," as used herein in relation to a bone plate, means to strengthen the bone plate such that the bone plate is more resistant to changes in its shape.

Connection sites 38, 40 may be provided by one or more pairs of aligned apertures of the bone plate and strut. Each pair of aligned apertures may receive a fastener 42, 44 (such as a threaded fastener) that holds the strut in place relative to the bone plate. Each individual aperture may be oblong, such as oblong aperture 46, or may be more symmetrical, such as underlying circular aperture 48 of the bone plate (see Section VII). The connection sites also may include and/or be associated with generally complementary engagement structures 50, 52, which may be formed in or near one or both connection sites. The generally complementary engagement structures may restrict slippage of the strut relative to the bone plate, particularly slippage parallel to a long axis defined by the strut (and/or bone plate). Furthermore, a complementary pair of engagement structures may fit together in only one register or may fit together in a plurality of discrete, alternative registers, particularly distinct longitudinal registers, to accommodate distinct bent configurations of the bone plate (and thus changes to the overall length of the bone plate). In other examples, engagement structures 50, 52 may be omitted to permit sliding of the strut relative to the bone plate after assembly of the bone plate and strut. Accordingly, the bone plate and strut may be assembled on bone, after the bone plate has been secured to bone, or off bone, before the bone plate has been secured to bone.

Further aspects of fixation system 20 are described elsewhere in the present teachings, for example, below in Section VII.

II. BONE PLATES

Bone plates generally comprise any relatively low-profile (plate-like) fixation device configured to stabilize at least one bone by attachment to the bone. The fixation device may be configured to span any suitable bone discontinuity (or discontinuities) so that the fixation device fixes the relative positions of bone portions/fragments (and/or bones) disposed on opposing sides of the bone discontinuity (or discontinuities). Alternatively, or in addition, the fixation device may reinforce a bone lacking a discontinuity.

Suitable discontinuities may occur naturally and/or may result from injury, disease, and/or surgical intervention, among others. Accordingly, exemplary discontinuities for use with the fixation devices described herein may include joints, fractures (breaks in bones), osteotomies (cuts in bones), and/or nonunions (for example, produced by injury, disease, or developmental defect), among others.

The bone plates described herein may be configured for use on any suitable bone, in any suitable species, including human, equine, canine, and/or feline species, among others. Exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, the mandible, the ribs, the sternum, and/or clavicles, among others.

Each bone plate may be an internal fixation device configured to be disposed at least mostly or completely internally during fixation. The bone plate thus may be disposed at least substantially or completely under the skin of a plate recipient after installation, generally such that the bone plate is apposed to, in contact with, and/or covers an exterior surface region of the bone. The installed bone plate thus may at least partially, at least mostly, or completely overlie bone and at least partially, at least mostly, or completely underlie soft tissue. The installed bone plate may be substantially, at least mostly, or completely outward of bone, or may extend into bone (e.g., a blade plate).

The bone plates may be formed of any suitable material(s) (see Section IV). These materials may provide the bone plate with a sturdy yet malleable construction. Generally, the bone plates (alone or in combination with a strut) should be stiffer and stronger than the section of bone spanned by the plates, yet flexible (e.g., springy) enough not to strain the bone significantly.

The bone plates may be configured to reduce irritation to the bone and surrounding tissue. For example, the bone plates may be formed of a biocompatible material, as described above. In addition, the bone plates may have a low and/or feathered profile to reduce protrusion of the bone plates into adjacent tissue and rounded, burr-free surfaces to reduce the effects of such protrusion.

The bone plates may be sized and shaped to conform to particular portions of a bone (or bones). The plates may be generally elongate, with a length L, a width W, and a thickness T. Here, length L≧width W>thickness T. In particular, the bone plates may be plate-like, with a length and width that are at least about two or five times greater than the bone plate thickness. In use, the long axis of the bone plates may be aligned substantially with the long axis of the corresponding bone, and/or may extend obliquely and/or transversely relative to the bone's long axis. The length and/or width of the bone plates may be varied according to the intended use, for example, to match the plates with a preselected region of bone(s) and/or a particular injury to the bone. For example, the plates may be generally linear for use on the shaft of a long bone and/or may have a nonlinear shape, such as for use near an end of a bone and/or for transverse placement on the shaft, among others. In some embodiments, the bone plates may be configured for use on both sides of the body/skeleton, such as when the bone plates are bilaterally symmetrical. In some embodiments, the bone plates may be asymmetrical, such that each bone plate is configured for use on either the left or the right side of the body/skeleton, but not both.

The bone plates may include inner (bone-facing) and outer (bone-opposing) faces (and/or surfaces). One or both of these faces may be contoured to follow an exterior surface region of a target bone (or bones) for which a bone plate is intended, so that the bone plate maintains a low profile and fits onto the bone(s). For example, the inner face of a bone plate may be substantially complementary in contour to the bone surface region, such as being concave to fit onto a convex bone surface region. The outer face of the plate also may correspond in contour to the bone surface region and may be generally complementary to the inner face of the plate, or may be distinct in contour. The bone plates may be at least partially shaped (pre-contoured) at the time of manufacture, allowing practitioners to apply them to bone(s) with less (or no) additional bending at the time of application. The bone plates thus may serve as templates for reconstructing damaged bones. Alternatively, or in addition, the bone plates may be custom-contoured by practitioners intraoperatively, namely, before, during, and/or after installation onto bone.

The thickness of the bone plates may be defined by the distance between the inner and outer faces of the plates. The thickness of the plates may vary between plates and/or within the plates, according to the intended use. For example, thinner plates may be configured for use on smaller bones and/or on bones or bone regions where soft tissue irritation is a greater concern. Thickness also or alternatively may vary along and/or across the plates. For example, the plates may become thinner as they extend over protrusions (such as processes, condyles, tuberosities, and/or the like), reducing their profile and/or rigidity, among others. The thickness of the plates also may be varied to facilitate use, for example, to make the plates thinner where they typically need to be deformed by bending the plates, such as at a junction (or bridge region) between plate portions. In this way, the plates may be thicker and thus stronger in regions where they may not need to be contoured (and/or are not stabilized by a strut). In some embodiments, the thickness of the plates may be determined, at least in part, by the region to be overlapped by a strut. For example, the plates may be thinner where they are overlapped by a strut and may be thicker elsewhere.

The bone plates may include one or more projections. The projections may extend, for example, generally inward from the inner face of the bone plates toward bone. Alternatively, or in addition, the projections may extend generally outward from the outer surface of the bone plates. The projections may be sharp or blunt according to their intended use. For examples, sharp projections may be configured as prongs that penetrate bone to restrict movement of the bone plates. Prongs may be used in place of, or in addition to, bone fasteners, for one or more portions of each bone plate. Blunt projections, such as ridges or knobs, may be configured to elevate the inner surface of the bone plates (and/or plate bodies) from the bone surface, for example, to allow space for tissue between the plates and bone and/or to decrease the effective stiffness of the bone plate. In some cases, the projections may facilitate assembly of a bone plate with a strut (e.g., see Section VII).

The bone plates each may include a plurality of apertures (openings). Each aperture may be threaded or nonthreaded, according to its intended use. Furthermore, each aperture may be non-elongate (e.g., circular or square) or elongate (e.g. oval or rectangular).

Further aspects of bone plates that may be suitable for strut-stabilized fixation are described in the following U.S. patent applications, which are incorporated herein by reference: Ser. No. 10/716,719, filed Nov. 19, 2003, now U.S. Pat. No. 7,090,676; Ser. No. 10/717,015, filed Nov. 19, 2003; Ser. No. 10/717,399, filed Nov. 19, 2003; Ser. No. 10/717,402, filed Nov. 19, 2003; Ser. No. 10/731,173, filed Dec. 8, 2003; Ser. No. 11/050,342, filed Feb. 2, 2005; Ser. No. 11/109,985, filed Apr. 19, 2005; Ser. No. 11/112,858, filed Apr. 22, 2005; Ser. No. 11/413,631, filed Apr. 28, 2006; Ser. No. 11/449,554, filed Jun. 7, 2006; Ser. No. 11/454,613, filed Jun. 16, 2006; and Ser. No. 11/486,959, filed Jul. 13, 2006.

III. STRUTS

The fixation systems of the present teachings include struts that assemble with bone plates to stabilize the bone plates. A "strut," as used herein, is any brace or other structural member that supports a bone plate, generally by resisting a tendency of the bone plate to bend under stress.

The struts may have any suitable shape and size. For example, the struts may have a length and a width that are substantially greater than the strut thickness, such as at least about two or five times as great, to provide a strut plate. Alternatively, the struts may have a width and a thickness that are about the same, to provide a strut rod. The struts may be substantially linear or may bend (angularly and/or arcuately), in plan and/or in profile. Furthermore, the struts may be branched or unbranched. Exemplary branched struts may be V-shaped, Y-shaped, U-shaped, V-shaped with a third arm disposed between the two arms of the V, and/or the like. The struts may have a substantially uniform width, or the width may vary along the length of the strut. Similarly, the struts may have a substantially uniform thickness, or may vary in thickness along the length and/or across the width of the struts. In exemplary embodiments, the struts are substantially linear when viewed in plan and in profile and have a substantially uniform thickness and width, with a thickness and/or width that is greater than the thickness and/or width of a corresponding bone plate. However, the struts may be thicker toward one or both opposing ends, such as to form engagement structure for mating with a bone plate. In other embodiments, the struts may have different profiles that match different bent configurations of a bone plate, such that a suitable strut (and strut profile) may be selected after a substantially final bent configuration of the bone plate has been produced intraoperatively.

The struts may have any suitable apertures (openings). The apertures may be through-holes extending between inner and outer surfaces of the struts. In addition, the apertures may be bounded circumferentially by an inner edge of the strut or may be bounded only partially by an outer edge of the strut, such that the apertures are open laterally. Each aperture may be threaded or nonthreaded, as appropriate. Furthermore, each aperture may be non-elongate (e.g., circular or square, among others) or elongate (e.g., oval or rectangular, among others).

Further aspects of auxiliary plates that may be suitable for use as struts in strut-stabilized fixation with bone plates are described in the following U.S. patent applications, which are incorporated herein by reference: Ser. No. 11/109,985, filed Apr. 19, 2005; and Ser. No. 11/112,858, filed Apr. 22, 2005.

IV. COMPOSITION OF SYSTEM COMPONENTS

Each system component (e.g., bone plate, strut, fasteners, etc.) may be formed of any suitable biocompatible and/or bioresorbable material(s). Exemplary biocompatible materials include (1) metals (for example, titanium or titanium alloys; alloys with cobalt and chromium (cobalt-chrome); stainless steel; etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites; (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-βhydroxypropionate, poly-δ-valerolactone, other bioresorbable polyesters, and/or natural polymers (such as collagen or other polypeptides, polysaccharides (e.g., starch, cellulose, and/or chitosan), any copolymers thereof, etc.); (6) bone tissue (e.g., bone powder and/or bone fragments); and/or the like. In some examples, these materials may form the body of a bone plate, strut, and/or fastener, and/or a coating thereon. The bone plate, strut, and fasteners of a fixation system may be formed of the same material(s) or different materials. Exemplary configurations with different materials may include a bone plate and a strut formed of different metals, such as a bone plate formed of a more malleable metal and a strut formed of a less malleable metal.

V. METHODS OF STRUT-STABILIZED BONE FIXATION

The strut-stabilized fixation systems of the present teachings may be installed by any suitable methods. Exemplary steps of the methods are listed below. These steps may be performed in any suitable order, in any suitable combination, and any suitable number of times.

A bone(s) to be fixed may be selected. The bone(s) may have any suitable injury, such as a fracture, a cut, a malunion, a nonunion, a developmental error, and/or the like. In some examples, the bone(s) selected may be two or more bones that articulate with one another through an anatomical joint. Any suitable anatomical joints may be selected, including the scapholunate joint, the acromioclavicular joint, the wrist, etc. Any suitable bone(s) may be selected for fixation, including a bone(s) of the hand (e.g., phalanges, metacarpals), wrist (e.g., carpal bones), arm (e.g., radius, ulna, humerus), foot (e.g. phalanges, metatarsals, tarsals), leg (e.g., femur, tibia, fibula, patella), shoulder (e.g. humerus, clavicle, scapula), etc. In exemplary embodiments, a radius bone may be selected. In particular, a radius bone having a distal fracture(s) may be selected.

A fixation device including a bone plate and a strut may be selected. The fixation device may have any combination of the features described elsewhere in the present teachings. Furthermore, the fixation device may have a size (e.g., length, width and/or thickness) and/or shape selected according to the size and/or shape of the target bone onto which the fixation device is to be installed. In some examples, selection of a fixation device may include selection of a suitable strut from a set of struts having different profiles. Accordingly, selection of the strut may be performed after the bone plate has been adjusted at least substantially to its final bent configuration. Selection of the fixation device may include selection of a bone plate and a strut that are not initially connected to one another or selection of a pre-assembled bone plate and strut (e.g., a slidably connected strut).

The fixation device may be installed on the selected bone (s). In particular, a bone plate of the fixation device may be secured to the selected bone. Securing the bone plate to the bone members and/or bone may include selecting one or more fasteners (e.g., bone screws, wires, pins, staples, etc.) and placing the one or more fasteners through openings defined by the bone plate. The openings may be disposed adjacent opposing sides of a discontinuity (e.g., a fracture) of the selected bone. Accordingly, placement of fasteners through the openings and into the selected bone may secure the bone plate to the bone on opposing sides of the discontinuity.

The bone plate may be secured to the selected bone with or without bending the bone plate prior to securing. For example, the bone plate may be manufactured with a linear profile and may be bent prior to application to bone, e.g., pre-operatively and/or intraoperatively, to approximate the profile of the target bone surface region to which the bone plate is to be applied. Alternatively, or in addition, the bone plate may be manufactured with a nonlinear profile that approximates the profile of a target surface region of bone to which the bone plate is to be secured.

In any case, the bone plate may be bent after it is secured to the selected bone, to adjust the shape of the bone plate. Bending the bone plate may introduce or alter a longitudinal bend in the bone plate, that is, a bend about an axis that is transverse to a regional and/or global long axis of the bone plate. Alternatively, or in addition, bending the bone plate may introduce a bend and/or twist in the bone plate about its long axis. Bending the bone plate may alter the bone plate from a linear profile to a bent profile, or may adjust the shape from one bent profile to another. In particular, bending may decrease or increase the distance between a pair of connection sites on the bone plate for attachment of the strut. Changes in the relative disposition of bone fragments produced by bending the bone plate may be visualized by any suitable approach. Exemplary approaches may include direct observation of the bone and/or bone fragments; direct observation of an anatomical structure (e.g., a limb) that includes or is connected to the bone and/or bone fragments; fluoroscopic observation of the bone and/or bone fragments; and/or the like.

The bone plate may be bent intraoperatively, while disposed on bone, by any suitable mechanism. The bone plate may be bent by direct manual engagement of the bone plate and/or connected bone, and/or by engagement with one or more tools. The tools may be structured to grip the bone plate, for example, with a clamp-like mechanism (e.g., pliers) or may be received in an opening(s) of the bone plate. In some embodiments, the one or more tools may be disposed in threaded engagement with one or more threaded openings of the bone plate, particularly threaded openings that flank a bending region of the bone plate. In any case, a deforming torque or other suitable force may be applied to the bone plate to create or alter a bend in the bone plate. The bone plate may be bent selectively in a region of the bone plate to be spanned by a strut.

A strut may be connected to the bone plate. Connecting the strut may be performed before and/or after the bone plate is secured to bone. If performed at least partially before the bone plate is secured to bone, the strut may be connected partially to the bone plate, for example, connected pivotably through only one connection site. This partial connection may be performed during manufacture of the bone plate and strut, pre-operatively after manufacture, and/or intraoperatively. If performed after the bone plate is secured to bone, the strut may be connected, in part, before the bone plate is bent on bone (e.g., at one connection site) or may be assembled with the bone plate only after bending the bone plate on bone has been completed. In other examples, the strut may be connected to a pair of connection sites, prior to securing the bone plate to bone (e.g., at the time of manufacture or pre-operatively, among others), such that the strut is slidable relative to one or both of the connection sites. Accordingly, the slidable strut may be fixed relative to the bone plate after the bone plate has been bent to a suitable configuration on bone.

The strut may be connected in any suitable position relative to the bone plate. The strut may be disposed mostly outward of and/or over the bone plate, mostly inward of and/or under the bone plate, at least partially inside the bone plate (e.g., extending into a cavity defined by the bone plate), and/or a combination of over, under, and/or inside the bone plate. The strut may overlap the bone plate substantially, for example, extending over (or under) at least a portion of a stem, body, and/or head of the bone plate. In some examples, the strut may define a long axis that is substantially centered over (or under) the stem, body, head, and/or central axis of the bone plate.

The strut may be connected to the bone plate by any suitable mechanism. For example, the strut may be connected by one or more fasteners that secure the strut to the bone plate. The fasteners may be threaded fasteners, such as screws, bolts, pins, etc. Other suitable fasteners may include wires, clamps, staples, rivets, suture material (or other thin cord), and/or the like. The fasteners may connect the strut only to the associated bone plate(s), or to a combination of the bone plate(s) and bone. The strut may be connected to the bone plate at any suitable number of positions, for example, at least two or exactly two spaced sites that flank a bending region of the bone plate.

The bone plate and/or strut may be left in place for any suitable period of time. In some examples, the bone plate and strut may be installed relatively permanently or indefinitely, and not removed surgically until desired or necessary (e.g., warranted for medical reasons). In some examples, the strut (or bone plate) may be removed selectively after a suitable time of healing, while leaving the bone plate (or strut) in place on bone. In some embodiments, both the bone plate and strut may be removed after a suitable period of fixation, or both may be left in place. The bone plate and/or strut may be absorbed by the body if one or both are formed of a bioresorbable material(s).

Further aspects of bending a bone plate disposed on bone are described in U.S. patent application Ser. No. 10/717,402, filed Nov. 19, 2003, which is incorporated herein by reference. In addition, further aspects of methods of fixation with a strut-stabilized bone plate and are described below in Example 2.

VI. KITS

The fixation systems of the present teachings may be provided in kits. The kits optionally may include (1) one or more bone plates, (2) one or more struts, (3) one or more fasteners for connecting the strut(s) to the bone plate, (4) fasteners for securing the bone plate(s) to bone, (5) drills and/or drivers for installing the fasteners (6) one or more tools for bending the bone plate(s) and/or strut(s) on bone and/or off bone, (7) a gauge for measuring the angular bend of the bone plate (and/or strut), and/or (8) instructions for use. Some or all of the components of the kit may be packaged in a sterile and/or sterilizable (e.g., autoclavable) condition. In some examples, components of the kit, such as the bone plate(s) and strut(s), may be intended for single use. In some examples, components of the kit, such as drills and/or drivers, may be intended or suitable for repeated use.

The kit may include a plurality of bone plates. The bone plates may substantially the same in size and/or shape, or may be different in size, shape, handedness (e.g., a left bone plate and a right bone plate), and/or pre-bent profile, among others.

The kit may include a plurality of struts. The struts of the kit may be substantially the same in size and/or shape, or may be a different in size (e.g., different lengths and/or widths), shape (e.g., linear, curved, branched, etc.), and/or pre-bent profile, among others. In some embodiments, the kit may include a plurality of struts that are manufactured to have different profiles (e.g., different bending angles) corresponding to different bent configurations of a bone plate. During use of the kit, an appropriate strut may be selected according to the extent to which the shape/profile of the bone plate has been adjusted before and/or after the bone plate has been secured to bone.

VII. EXAMPLES

The following examples describe selected aspects and embodiments of systems for strut-stabilized bone fixation. These examples are included for illustration and are not intended to limit or define the entire scope of the present teachings.

Example 1

Exemplary System for Strut-Stabilized Bone Fixation

This example describes selected aspects of an exemplary fixation system 20 for strut-stabilized fixation of bones, particularly stabilization of a distal portion of a radius bone; see FIGS. 2-6. Fixation system 20 was introduced above in Section I, with reference to FIG. 1.

Figure 2:
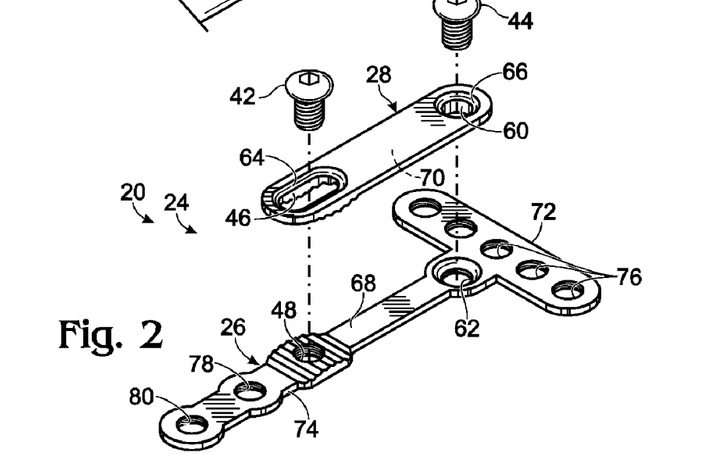
FIG. 2 is an exploded view of the fixation system of FIG. 1 in the absence of bone.

FIG. 2 shows an exploded view of fixation system 20. Bone plate 26 and strut (or strut plate) 28 may define one or more pairs of elongate and/or non-elongate apertures for receiving fasteners that secure the strut to the bone plate. For example, here, the bone plate and strut define two pairs of aligned apertures: strut 28 defines elongate aperture 46 and a circular aperture 60 that align, respectively, with aperture 48 and aperture 62 of the bone plate.

Each of apertures 46 and 60 of the strut may have any suitable structure. The strut apertures may be nonthreaded or threaded internally, as appropriate, and may include respective countersinks 64, 66 for receiving at least a portion of the head of fasteners 42, 44.

Apertures 48, 62 of the bone plate also may have any suitable structure. These bone plate apertures, used for connection of the strut (and/or engagement with a bending tool (s)), may be threaded internally, to provide threaded engagement with threaded fasteners 42, 44 that couple the strut to the bone plate. However, in some embodiments, these apertures of the bone plate may be nonthreaded, such that engagement of fasteners with underlying bone is used to hold the fasteners (and strut) in place. Accordingly, one or both of fasteners 42, 44 may be relatively short, such that the fasteners extend through the strut and into apertures of the bone plate, but not into bone, or may be relatively long and, for example, structured as bone screws, such that the fasteners extend through the strut, through the bone plate, and thread into bone (and optionally the bone plate, too).

Strut 28 may have any suitable disposition relative to bone plate 26. Here, strut 28 is disposed generally outward of the bone plate, with an outer face 68 of the bone plate disposed adjacent an inner face 70 of the strut. However, in other arrangements, the strut may be disposed generally inward of the bone plate, with an outer face of the strut disposed adjacent an inner face of the bone plate.

Strut 28 may be coupled to the bone plate at any suitable position along and/or across the bone plate. For example, here, strut 28 is coupled at a central region of the T-shaped bone plate, proximal to a head 72 of the bone plate, and distally along a stem 74 extending from the head. However, in other arrangements, the strut may be disposed more proximally and/or more distally, such as by using one or more of head apertures 76 and/or distal stem apertures 78, 80 for connecting the strut to the bone plate, and/or by increasing (or decreasing) the length of the strut. Furthermore, the strut may be aligned with and/or oblique (or orthogonal to) to any suitable axis of the bone plate. Here, the strut is centered transversely on the bone plate, overlying a distal region of the stem of the bone plate, and generally parallel to a central long axis defined by the stem. In other examples, the strut may be offset laterally from the stem and/or oriented obliquely to the stem, such as coupled to the stem and a head aperture(s) 76 that is laterally offset in either lateral direction from the stem. In some cases, the strut may be disposed transversely (e.g., orthogonally) to the long axis of the bone plate.

Figure 3:
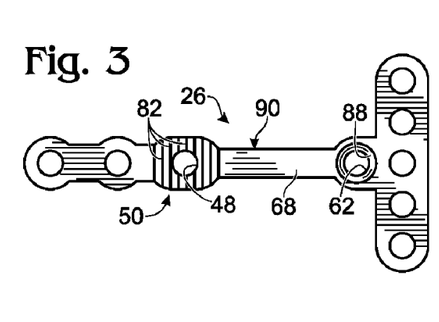
FIG. 3 in a plan view of the bone plate of FIG. 1.
Figure 4:
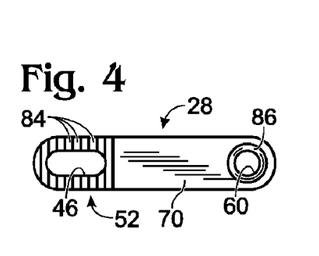
FIG. 4 is a bottom view of the strut of FIG. 1.

FIGS. 3 and 4 show top and bottom views, respectively, of bone plate 26 and strut 28. Moreover, these views show generally complementary engagement structures of the bone plate and strut that engage one another when the strut is connected to the bone plate.

Proximal engagement structures 50, 52 may be defined, respectively, by outer face 68 of the bone plate and inner face 70 of strut 28. The proximal structures may, for example, be a set of ridges (and/or grooves) 82 of the bone plate that mate with (are received by) a corresponding set of grooves (and/or ridges) 84 of the strut. The ridges and/or grooves (and/or other suitable projection/depressions) may be spaced uniformly such that proximal engagement structures 50, 52 may be engaged in different discrete registers, to provide incremental changes in the relative longitudinal positions of elongate aperture 46 of the strut along the stem of the bone plate (also compare FIGS. 5 and 6). In other embodiments, the strut may slide readily along the surface of the bone plate, such that the strut is adjustable over a continuous range of longitudinal positions.

Distal engagement structures 86, 88 may be defined, respectively, by a projection (or depression) of inner face 70 of strut 28 received in a depression (or projection) of outer face 68 of bone plate 26. More particularly, distal aperture 60 of the strut may be concentric with distal engagement structure 86, which may be formed as a spherically shaped (e.g., frustospherical) projection from the body of the strut. Similarly, distal aperture 62 of the bone plate may be concentric with a spherically shaped (e.g., frustospherical) concavity or depression formed in the outer face of the bone plate. Furthermore, distal engagement structures 86, 88 may be sized such that the strut can pivot about a transverse axis, to accommodate distinct bent configurations of bone plate 26 (e.g., compare FIGS. 5 and 6).

Bone plate 26 and strut 28 may have any suitable widths. For example, bone plate 26 may have a bending region, indicated at 90, disposed between apertures 48 and 62 (and thus between sites at which the strut is connected to the bone plate). The bending region may be narrower, thinner, and/or formed of a more malleable material than other regions of the bone plate, particularly the remainder of the stem and/or the head of the bone plate. (The bending region may be rendered more malleable by selective treatment (heating, cooling, pressing, working, etc.) of a section of the bone plate.) Furthermore, the bending region may extend along any suitable portion of the stem and/or bone plate, for example, less than about one-half, about one-half, or greater than about one-half of the length of the stem and/or bone plate. The strut may have a width that is about the same as or different from the bone plate and/or bending region. For example, here, the strut is wider than the bending region and about the same width as other regions of the bone plate. In other embodiments, the strut may be substantially wider than (or narrower than) the average and/or maximum width of the stem and/or bone plate.

Figure 5:
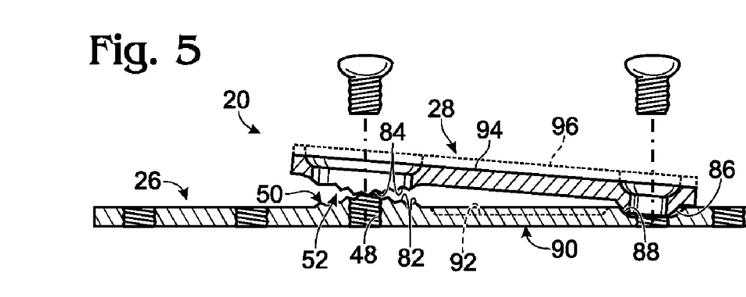
FIG. 5 is a sectional, partially exploded view of the fixation system of FIG. 1, taken generally along line 5-5 of FIG. 1 in the absence of bone and with the bone plate in an initial (e.g., planar or less-bent) configuration, in accordance with aspects of the present teachings.

FIG. 5 shows a sectional, partially exploded view of fixation system 20 with bone plate 26 in an initial (e.g., less-bent) configuration. The bone plate thus may be manufactured to have a planar configuration (a linear or unbent profile), as shown here, or may be manufactured in a pre-bent configuration, with a nonlinear or bent profile, for example, to approximately match the contour(s) of a surface region of target bone. In exemplary embodiments, the bone plate may be manufactured (and/or bent pre-operatively or intraoperatively) to impart a concave (or convex) shape longitudinally to the outer face of the bone plate (e.g., see the concave configuration of FIG. 6).

The bone plate and strut may have any suitable thicknesses. For example, bone plate 26 may have a relatively uniform thickness along the length of the bone plate. Alternatively, bone plate 26 may be thinner, indicated by a dashed line at 92, in bending region 90 relative to other portions of the stem and/or the head of the bone plate. Furthermore, the strut may be about the same thickness as the bone plate and/or the bending region, as illustrated by the solid perimeter line at 94, or may be thicker than the bending region and/or bone plate, as indicated by a dashed line at 96. In addition, the bone plate and/or strut may vary in thickness to create proximal and/or distal engagement structures (50, 52, 86, and/or 88). For example, ridges 82 and/or the intervening grooves may be arranged on a generally projecting surface region of the bone plate, as shown in FIG. 5, to create a generally thickened region of the bone plate around aperture 48. Alternatively, ridges, grooves (and/or other mating/engagement structure) may be formed by a region of the bone plate (and/or strut) that is about the same thickness or of lesser thickness than other regions of the bone plate (and/or strut). Accordingly, the mating structure may be disposed in a depressed area of the bone plate (and/or strut). Generally, it may be desirable to minimize any unnecessary increases in combined thickness of the bone plate and strut created by complementary engagement structures.

Figure 6:
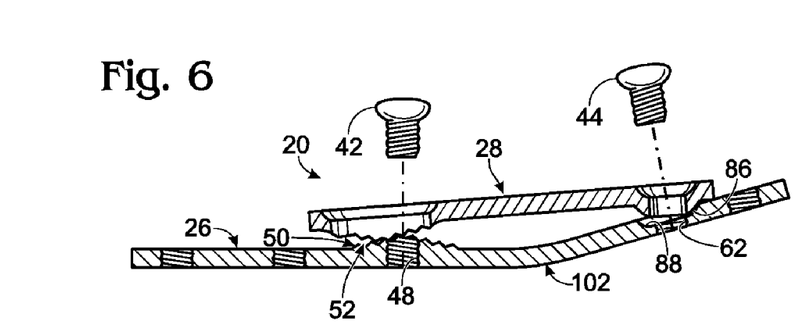
FIG. 6 is a sectional, partially exploded view of the fixation system of FIG. 1, taken as in FIG. 5, but with the bone plate bent from the initial configuration of FIG. 5, in accordance with aspects of the present teachings.

FIG. 6 shows a sectional, partially exploded view of fixation system 20 with bone plate 26 bent from the initial configuration of FIG. 5 (e.g., bent prior to assembly of the bone plate and strut). Engagement structures 50, 52 may be mated in a different register than that of FIG. 5 to accommodate a decrease in linear spacing between apertures 48 and 62 created by a transverse bend 102 in the bone plate. Accordingly, the proximal and distal engagement structures may restrict relative longitudinal motion (namely, slippage) of the bone plate and strut before, during, and/or after fasteners 42, 44 are installed. In any case, the strut may extend generally parallel to a long axis of the bone plate such that the bone plate may be restricted from bending motion that would increase or decrease the spacing between apertures 48 and 62. The strut thus may have a generally linear profile, as shown here, to maximize resistance to bending of the bone plate. Alternatively, the strut may be manufactured and/or bent pre-operatively/intraoperatively to have a bent profile that, for example, provides better correspondence between the profiles of the bone plate and strut, thereby minimizing protrusion of the strut (particularly centrally along the strut) into overlying soft tissue.

Example 2

Exemplary Method of Bone Fixation with a Bone Plate and Strut

This example describes an exemplary method of fixing a bone using a fixation device including a bone plate and strut; see FIGS. 7-10. The exemplary method is illustrated here using fixation system 20 (see FIGS. 1-6). However, any other suitable bone plate and strut may be used on any suitable bone having any suitable indication.

Figure 7:
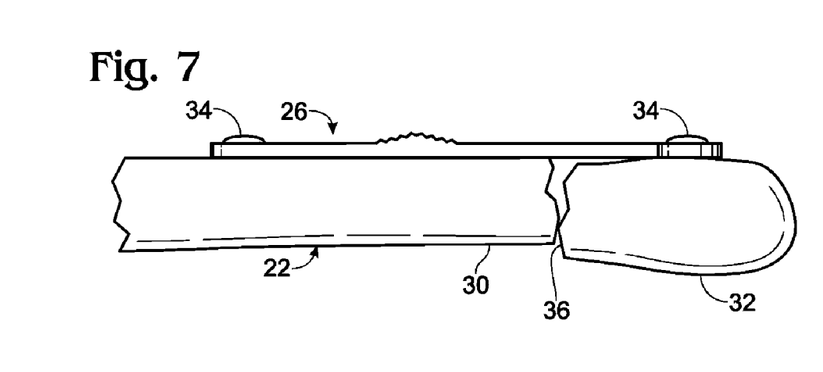
FIGS. 7-10 are a series of medial-distal views of a fractured radius bone in exemplary configurations produced by performing a method of fixing a bone with the bone plate and strut of FIG. 1, in accordance with aspects of the present teachings.

FIG. 7 shows bone plate 26 secured to fractured radius 22 using bone screws 34. The bone plate may span fracture 36 with bone screws placed through openings of the bone plate and into proximal fragment(s) 30 and distal fragment(s) 32 of the fractured radius. The bone plate may be disposed adjacent and/or may abut any suitable surface of the radius, such as a volar or dorsal surface of a distal portion of the radius.

Any suitable number of bone screws may be placed into bone on opposing sides of a discontinuity in the radius. However, in the present example, at least one bone screw (or other fastener) secures a proximal portion (e.g., a stem) and at least one bone screw (or other fastener) secures a distal portion (e.g., a head) of the bone plate to bone.

The fractured radius may be reduced before and/or during attachment of the bone plate to the radius, to approximately restore the anatomical (pre-fracture) alignment of proximal and distal fragments 30, 32. In any event, the bone plate may have a linear profile when installed initially on the bone, or may have a bent profile that approximates a longitudinal profile of a target surface region of the radius bone. Furthermore, the bone plate may have rounded and/or feathered edges to reduce irritation of overlying soft tissue, and protrusion of the heads of bone screws 34 above the bone plate may be minimized for the same reason.

Figure 8:
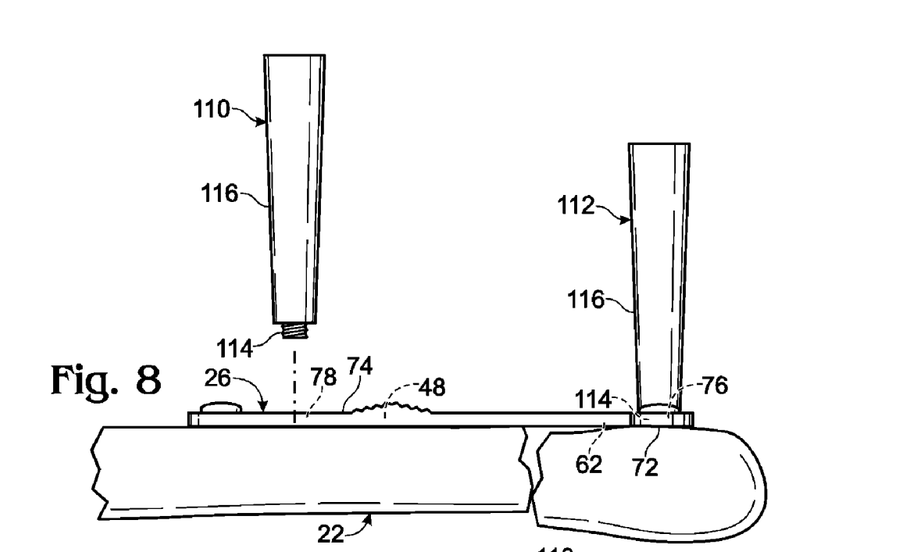

FIG. 8 shows bone plate 26 secured to fractured radius 22 during connection of bending tools 110, 112 to the bone plate. Each bending tool may have a threaded (or nonthreaded) section 114 disposed adjacent a leading end of the tool and a handle section 116 connected to the threaded section. The threaded section of a bending tool may be structured for threaded engagement with a threaded aperture(s) of the bone plate (or nonthreaded insertion into a threaded or nonthreaded aperture of the bone plate). For example, here, bending tool 110 is positioned for advancement into, and threaded engagement with, threaded aperture 78 of stem 74 of the bone plate, and bending tool 112 already is in threaded engagement with a central threaded aperture 76 of head 72. However, in other examples, bending tools 110, 112 may be coupled to the bone plate via one or both of threaded (or nonthreaded) apertures 48, 62 of the bone plate, which are included in the connection sites through which the strut is connected to the bone plate via fasteners.

Figure 9:
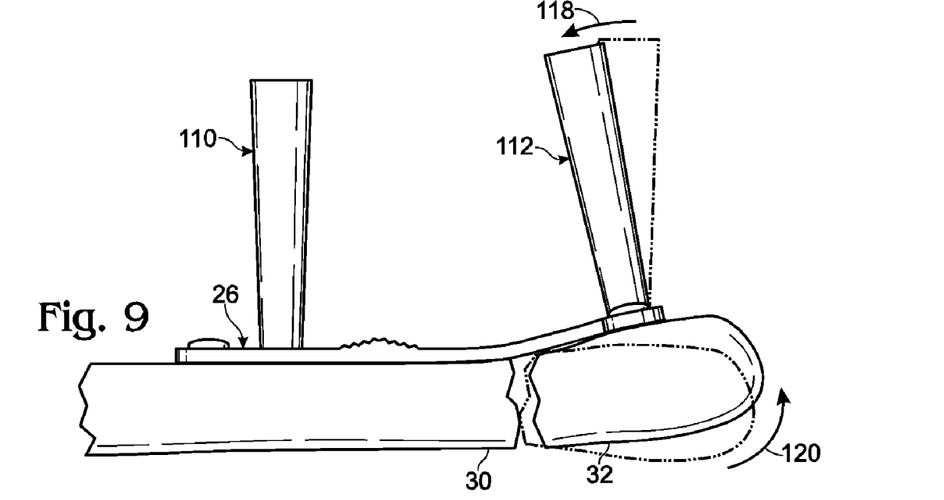

FIG. 9 shows bone plate 26 in a longitudinally bent configuration created by application of a torque, indicated at 118, to the bone plate via bending tools 110, 112. The bent configuration of the bone plate created by the bending tools produces a change in the angular disposition of distal fragment 32 relative to proximal fragment 30, indicated at 120.

Figure 10:
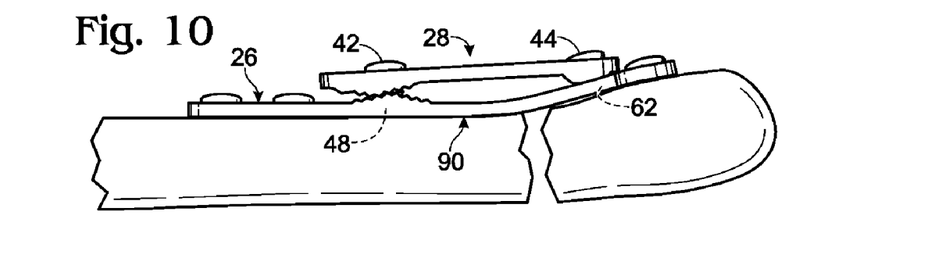

FIG. 10 shows bone plate 26 in the bent configuration of FIG. 9 and assembled with strut 28, to stabilize the bent configuration. Fasteners 42, 44 may be installed in two pairs of aligned apertures of the strut and the bone plate at a pair of connection sites flanking bending region 90 of the bone plate. Bending tools 110, 112 (see FIGS. 8 and 9) have been removed in this view. However, because apertures of the bone plate are being used here that are outside of the strut footprint on the bone plate, in some embodiments, the bending tools may be left in place until the strut is fully secured to the bone plate, to allow final adjustments to the bent configuration of the bone plate. In contrast, if strut-coupling apertures 48 and 62 are used to receive the bending tools, the bending tools generally are removed prior to assembly of the strut with the bone plate.

The bending tools may have any suitable structure. For example, the bending tools may be nonthreaded distally for nonthreaded engagement with apertures of the bone plate. In other embodiments, the bending tools may, for example, include jaws or opposing hooks that engage the sides of the bone plate. The bending tools may be of any suitable length, particularly a length that allows application of a sufficient torque manually (e.g., via the hand(s) of a surgeon). In exemplary embodiments, the bending tools may be at least about five, ten, or twenty centimeters in length and/or at least about as long as, or two, five, or ten times as long as the length of the bending region (of the bone plate) that the bending tools flank. The handle section of each bending tool may be structured to facilitate manual engagement. Accordingly, the handle section may be ribbed, knurled, flanged, knobbed, and/or the like.

Example 3

Selected Embodiments I

This example describes exemplary features of a strut connected to a bone plate. The strut may include any suitable combination of the following features. The strut may connect between two (or more) regions of the bone plate. The strut may connect within a portion of the footprint of the bone plate. The strut may not connect to bone independent of the bone plate. The strut may not directly contact bone. The strut may substantially overlap a portion of the bone plate. The strut may be aligned with the long axis of bone. The strut may connect to the bone plate on opposite sides of an injury to bone. The strut may connect to the bone plate on opposite sides of a bend in the bone plate (and/or a bending region of the bone plate at which the bone plate is bent selectively to create a bent configuration). At least a central region of the strut may be spaced from the bone plate when connected to the bone plate.

Example 4

Selected Embodiments II

This example describes selected embodiments of the present teachings, presented as a series of indexed paragraphs.

1. A system for bone fixation, comprising: (A) a bone plate; and (B) a strut that connects to the bone plate intraoperatively to stabilize each of a plurality of alternative bent configurations of the bone plate produced by bending the bone plate to different extents about one or more transverse axes of the bone plate.

2. The system of paragraph 1, wherein the strut connects to the bone plate using fasteners placed at two or more spaced locations defined by the strut, the bone plate, or both.

3. The system of paragraph 1 or 2, wherein the bone plate is structured to be secured to a distal portion of a radius bone.

4. The system of any of paragraphs 1-3, wherein the bone plate and the strut are configured to engage one another in two or more discrete registers, to stabilize distinct bent configurations of the bone plate.

5. The system of any of paragraphs 1-4, wherein the bone plate and the strut engage one another via an array of projections formed on an outer face of the bone plate, an inner face of the strut, or both.

6. The system of any of paragraphs 1-5, wherein the strut has a plate structure.

7. The system of any of paragraphs 1-6, wherein the strut defines at least two openings for receiving fasteners that connect the strut to the bone plate.

8. The system of any of paragraphs 1-7, wherein the bone plate is generally T-shaped.

9. The system of any of paragraphs 1-8, wherein the bone plate is configured to be bent selectively in a central region of the bone plate.

10. The system of any of paragraphs 1-9, wherein the bone plate and the strut each define a pair of openings, and wherein the pair of openings of the strut are configured to be aligned with the pair of openings of the bone plate for receiving fasteners that connect the strut to the bone plate.

11. The system of any of paragraphs 1-10, wherein the strut is thicker than the bone plate.

12. The system of any of paragraphs 1-11, further comprising fasteners for connecting the strut to the bone plate.

13. The system of paragraph 12, wherein the strut, the bone plate, or both are configured for threaded engagement with the fasteners.

14. The system of any of paragraphs 1-13, wherein the strut connects to the bone plate adjacent an outer face of the bone plate.

15. A system for bone fixation, comprising: (A) a bone plate; and (B) a strut that connects to the bone plate using fasteners placed at two or more spaced locations defined by the strut, the bone plate, or both, to stabilize each of a plurality of alternative bent configurations of the bone plate.

16. The system of paragraph 15, wherein the bone plate and the strut are configured to engage one another in two or more discrete registers, to stabilize distinct bent configurations of the bone plate.

17. The system of paragraphs 15 or 16, wherein the strut defines at least two openings for receiving the fasteners.

18. The system of any of paragraphs 15-17, wherein the strut, the bone plate, or both are configured for threaded engagement with the fasteners.

19. A system for bone fixation, comprising: (A) a bone plate; and (B) a strut that connects to the bone plate in two or more discrete, alternative registers to stabilize distinct bent configurations of the bone plate.

20. The system of paragraph 19, wherein the bone plate and the strut engage one another in the two or more discrete, alternative registers via an array of projections formed on an outer face of the bone plate, an inner face of the strut, or both.

21. A method of bone fixation, comprising: (A) securing a bone plate to at least one bone; (B) bending the bone plate to a bent configuration while the bone plate is secured to the bone; and (C) connecting a strut to the bone plate such that the bent configuration is stabilized.

22. The method of paragraph 21, wherein the step of securing includes a step of securing the bone plate to a distal portion of a radius bone.

23. The method of paragraph 22, wherein the step of securing includes a step of securing the bone plate adjacent a volar surface of the distal portion of the radius bone.

24. The method of any of paragraphs 21-23, the strut defining one or more apertures, wherein the step of connecting includes a step of placing one or more fasteners through at least one of the apertures.

25. The method of paragraph 24, wherein the step of placing includes a step of placing at least one bone screw through the bone plate and into the at least one bone.

26. The method of any of paragraphs 21-24, further comprising a step of bending the bone plate before the step of securing.

27. The method of any of paragraphs 21-26, wherein the step of bending the bone plate while the bone plate is secured to the bone includes a step of applying a torque to the bone plate via at least one tool engaged with the bone plate.

28. The method of paragraph 27, wherein the step of bending includes a step of bending the bone plate selectively within a region along the bone plate, further comprising a step of disposing the bone plate in engagement with the at least one tool at spaced sites flanking the region at which the bone plate is to be bent selectively.

29. The method of any of paragraphs 21-28, the strut being a strut plate, the bone plate and the strut plate each having opposing inner and outer faces, wherein the step of connecting includes a step of disposing the inner face of the strut plate adjacent the outer face of the bone plate.

30. The method of any of paragraphs 21-29, wherein the bone plate and strut have generally complementary engagement structures that fit together in two or more discrete registers, and wherein the step of connecting includes (1) a step of selecting a register for the engagement structures and (2) a step of coupling the strut to the bone plate in the register selected.

31. The method of any of paragraphs 21-30, wherein the step of connecting includes a step of connecting the strut to the bone plate by placing fasteners into at least two pairs of aligned apertures provided by the bone plate and strut.

32. The method of any of paragraphs 21-31, each of the bone plate and the strut defining a long axis, wherein the step of connecting includes (1) a step of disposing the long axes of the bone plate and strut generally parallel to one another and (2) a step of coupling the strut to the bone plate after the step of disposing.

33. The method of paragraph 32, wherein the step of disposing includes a step of disposing the strut in a position that is substantially centered transversely in relation to the bone plate.

34. A method of bone fixation, comprising: (A) bending a bone plate to a bent configuration intraoperatively; (B) securing the bone plate to a bone; and (C) connecting a strut to the bone plate such that the bent configuration is stabilized.

35. The method of paragraph 34, wherein the step of connecting is performed with threaded fasteners.

36. The method of paragraph 34 or 35, the bone plate having a long axis, wherein the step of bending is performed about one or more axes that are transverse to the long axis.

37. The method of any of paragraphs 34-36, wherein the step of connecting includes a step of connecting a strut having a linear profile.

38. The method of any of paragraphs 34-37, wherein the step of bending is performed with one or more tools disposed in threaded engagement with the bone plate.

39. The method of any of paragraphs 34-38, wherein the step of connecting includes a step of connecting the strut to the bone plate at two or more spaced positions of the bone plate.

40. The method of any of paragraphs 34-39, wherein the step of bending includes a step of bending the bone plate selectively in a region of the bone plate, and wherein the step of connecting includes a step of connecting a strut to the bone plate such that the strut spans the region in which the bone plate is bent selectively.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of bone fixation, comprising:
attaching a bone plate to a bone;
deforming a monolithic region of the bone plate to a deformed configuration after attaching the bone plate to the bone; and
connecting a strut plate to the bone plate with the strut plate spanning the monolithic region, to form an assembly that stabilizes the deformed configuration,
wherein the monolithic region has an inner surface area that faces the bone and that defines an axis substantially centered within and substantially orthogonal to the inner surface area, and wherein a thickness of the strut plate measured along the axis is greater than a thickness of the bone plate measured along the axis in the assembly
wherein a region of the strut plate overlying the monolithic region in the assembly is separated from the monolithic region along the axis to form a gap between the strut plate and the bone plate.

2. The method of claim 1, wherein the gap has a size measured along the axis, and wherein the size of the gap is greater than the thickness of the bone plate.

3. The method of claim 1, wherein the gap has a size measured along the axis, and wherein the step of deforming determines the size of the gap.

4. The method of claim 1, wherein the monolithic region has an outer surface area opposite the inner surface area and defining a plane, and wherein a complete transverse section of the strut plate taken at the axis does not cross the plane.

5. The method of claim 1, wherein the bone plate and the strut plate each include an engagement structure, wherein the engagement structures of the bone plate and the strut plate are at least generally complementary to one another and fit together in only a finite number of discrete, alternative registers that provide incremental changes in a position of the strut plate with respect to the bone plate, and wherein the step of connecting includes (1) a step of selecting a register for the engagement structures and (2) a step of connecting the strut plate to the bone plate in the register selected.

6. The method of claim 5, wherein the bone plate defines a longitudinal axis, wherein one of the engagement structures includes a plurality of ridges and the other of the engagement structures includes a plurality of grooves, and wherein each ridge and each groove extends perpendicular to the longitudinal axis when the engagement structures fit together in each register.

7. The method of claim 1, wherein the step of deforming is performed with one or more tools disposed in threaded engagement with the bone plate.

8. The method of claim 1, wherein the step of connecting includes a step of disposing at least one fastener in threaded engagement with the bone plate.

9. The method of claim 1, wherein the bone plate is attached to a distal portion of a radial bone.

10. The method of claim 1, wherein the step of connecting includes a step of connecting the strut plate to the bone plate by placing fasteners into at least two pairs of aligned apertures provided by the bone plate and the strut plate.

11. The method of claim 1, wherein the strut plate defines a longitudinal axis, wherein the step of connecting includes a step of placing a fastener through an aperture of the strut plate, and wherein the aperture is elongated substantially parallel to the longitudinal axis.

12. A method of bone fixation, comprising:
attaching a bone plate to a bone;
deforming a monolithic region of the bone plate to a deformed configuration after attaching the bone plate to the bone; and
connecting a strut plate to the bone plate with the strut plate spanning the monolithic region, to form an assembly that stabilizes the deformed configuration,
wherein the monolithic region has an inner surface area that faces the bone and an outer surface area opposite the inner surface area and defining a plane, wherein the outer surface area also defines an axis substantially centered within and substantially orthogonal to the outer surface area, and wherein a complete transverse section of the strut plate taken at the axis is disposed on only one side of the plane,
wherein a region of the strut plate overlying the monolithic region in the assembly is separated from the monolithic region along the axis to form a gap between the strut plate and the bone plate.

13. The method of claim 12, wherein the gap has a size measured along the axis, and wherein the size of the gap is greater than a thickness of the bone plate measured along the axis.

14. The method of claim 12, wherein the gap has a size measured along the axis, and wherein the step of deforming determines the size of the gap.

15. A method of bone fixation, comprising:
attaching a bone plate to a bone;
deforming a monolithic region of the bone plate to a deformed configuration after attaching the bone plate to the bone; and
connecting a strut plate to the bone plate with the strut plate spanning the monolithic region, to form an assembly that stabilizes the deformed configuration,
wherein the monolithic region has an inner surface area that faces the bone and that defines an axis substantially centered within and substantially orthogonal to the inner surface area, and wherein a region of the strut plate overlying the monolithic region in the assembly is separated from the monolithic region along the axis to form a gap between the strut plate and the bone plate.

16. The method of claim 15, wherein the gap has a size measured along the axis, and wherein the size of the gap is greater than a thickness of the bone plate measured along the axis.

17. The method of claim 15, wherein the gap has a size measured along the axis, and wherein the step of deforming determines the size of the gap.

18. The method of claim 15, wherein the bone plate is attached to a distal portion of a radial bone.

* * * * *